(12) United States Patent
Kuwabara et al.

(10) Patent No.: US 6,908,754 B2
(45) Date of Patent: Jun. 21, 2005

(54) CARBAMOYL-PHOSPHATE SYNTHETASE GENE OF CORYNEFORM BACTERIA AND METHOD FOR PRODUCING L-ARGININE

(75) Inventors: Yoko Kuwabara, Kawasaki (JP); Kenichi Hashiguchi, Kawasaki (JP); Tsuyoshi Nakamatsu, Kawasaki (JP); Osamu Kurahashi, Kawasaki (JP); Yukiko Mori, Kawasaki (JP); Hisao Ito, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 380 days.

(21) Appl. No.: 10/284,334

(22) Filed: Oct. 31, 2002

(65) Prior Publication Data

US 2003/0082775 A1 May 1, 2003

Related U.S. Application Data

(62) Division of application No. 09/494,359, filed on Jan. 31, 2000, now abandoned.

(30) Foreign Application Priority Data

Feb. 1, 1999 (JP) .............................. 11-24149

(51) Int. Cl.[7] .............................. C12N 9/10; C12N 9/12; C07K 17/00
(52) U.S. Cl. ........................ 435/193; 435/194; 530/350
(58) Field of Search ................................ 435/193, 194, 435/252.3, 252.33; 530/350; 536/23.2, 23.7

(56) References Cited

U.S. PATENT DOCUMENTS 6,255,086 B1  7/2001  Kuwabara et al. .......... 435/114

FOREIGN PATENT DOCUMENTS

| EP | 0 077 548 | 4/1983 |
| EP | 0 261 6627 | 3/1988 |
| WO | WO 95/03417 | 2/1995 |

OTHER PUBLICATIONS

M. Crabeel, et al., Journal of Bacteriology, vol. 143, No. 2, pp. 921–925, "use of Gene Cloning to Determine Polarity of an Operon: Genes Carab of *Escherichia coli*", Aug. 1980.

M. Mergeay, et al., Molec. Gen. Genet., pp. 299–316, "Physiology and Genetics of Carbamoylphosphate Syntesis in *Escherichia coli* K12", 1974.

(Continued)

*Primary Examiner*—Nashaat T. Nashed
(74) *Attorney, Agent, or Firm*—Oblon, Spivak, McClelland, Maier & Neustadt, P.C.

(57) ABSTRACT

A DNA fragment which encodes a polypeptide defined in the following (a) or (b), and a polypeptide defined in the following (c) or (d):

(a) a polypeptide which has at least the amino acid sequence of the amino acid numbers 50 to 393 in SEQ ID NO: 2 shown in Sequence Listing,
(b) a polypeptide which has at least the amino acid sequence of the amino acid numbers 50 to 393 in SEQ ID NO: 2 shown in Sequence Listing including substitution, deletion, insertion, addition, or inversion of one or several amino acids, and can constitute a protein having a carbamoyl-phosphate synthetase activity with a large subunit of carbamoyl-phosphate synthetase having the amino acid sequence of SEQ ID NO: 3,
(c) a polypeptide which has the amino acid sequence of SEQ ID NO: 3 shown in Sequence Listing,
(d) a polypeptide which has the amino acid sequence of SEQ ID NO: 3 shown in Sequence Listing including substitution, deletion, insertion, addition, or inversion of one or several amino acids, and can constitute a protein having a carbamoyl-phosphate synthetase activity with a small subunit of carbamoyl-phosphate synthetase having the amino acid sequence of the amino acid numbers 50 to 393 in SEQ ID NO: 2.

6 Claims, 2 Drawing Sheets

OTHER PUBLICATIONS

J. Piette, et al., Proc. Natl. Acad. Sci. USA, vol. 81, pp. 4134–4138, "DNA Sequence of the Cara Gene and the Control Region of Carab: Tandem Promoters, Prespectively Controlled by Arginine and the Pyrimidines, Regulate the Systhesis of Carbamoyl–Phosphate Synthetase in *Escherichia coli* K–12", Jul. 1984.

H. Yang, et al., Eur. J. Biochem. vol. 249, pp. 443–449, "Cloning and Characterization of the Arginine–Specific Carbamoyl–Phosphate Synthetase from *Bacillus stearothermophilus*", 1997.

M. Tuchman, et al. Applied and Environmental Microbiology, vol. 63, No. 1, pp. 33–38 "Enhanced Production of Arginine and Urea by Genetically Engineered *Escherichia coli* K–12 Strains", Jan. 1997.

G. Deckert, et al., Carbamoyl Phosphate Synthetase Small Subunit, 1 page, "the Complete Genome of the Hyperthermophilic Bacterium *Aquifex aeolicus*," Aug. 1, 1998, Database:EMBL, Accession No. 066727.

S. Tabata, Carbamoyl–phosphate Synthease, Pyrimidine–specific, Large Chain, 2 pages, "Sequence Analysis of the Genome of the Unicellular Cyanobacterium," Biv, 1, 1996, Database EMBL, Accession No. Q55756.

K. Matsui, et al., Agricultural and Biological Chemistry, vol. 51, No. 3, pp. 823–828, XP–001160768, "Cloning of Tryptophan Genes of Brevibacterium Lactofermentum, A Glutamic Acid–Producing Bacterium", 1987.

J. P. Schofield, et al., Clinical Science, Biochemical Society and the Medical Research Society, vol. 84, No. 2, pp. 119–128, XP–002038834, "Molecular Studies on an Ancient Gene Encoding for Carbamoyl–Phosphate Synthetase", Aug. 25, 1997.

F. S. Lawson, et al., Microbiology, vol. 141, pp. 1183–1191, XP–008020579, "Organization of Carbamoyl–Phosphate Synthase Genes in *Neisseria Gonorrhoeae* Includes a Large, Variable Intergenic Sequence Which is also Present in Other *Neisseria* Species", 1995.

A. Elagöz, et al., Gene an International Journal on Genes and Genomes, vol. 182, pp. 37–43, "Structure and Organisation of the Pyrimidine Biosynthesis Pathway Genes in *Lactobacillus plantarum*: a PCR Strategy for Sequencing Without Cloning", Dec. 1996.

M. Kilstrup, et al., Database Biosis, Biological Abstracts Inc., US, Biosis, 1 page, an Prev198886113458, "Nucleotide Sequence of the Cara Gene and Regulation of Carab Operon in *Salmonella–typhimurium*", 1988.

H. Yang, et al., Database Biosis, Biological Abstracts Inc., US, Biosis, 2 pages an Prev 199799812800, "Cloning and Characterization of the Arginine–Specific Carbamoyl–Phosphate Synthetase from *Bacillus Stearothermophilus*", 1997

SEQUENCE LISTING

<160> NUMBER OF SEQ ID NOS: 7

<210> SEQ ID NO 1
<211> LENGTH: 4837
<212> TYPE: DNA
<213> ORGANISM: Brevibacterium lactofermentum
<220> FEATURE:
<221> NAME/KEY: CDS
<222> LOCATION: (283)..(1461)
<223> OTHER INFORMATION:
<220> FEATURE:
<221> NAME/KEY: CDS
<222> LOCATION: (1470)..(4808)
<223> OTHER INFORMATION:

<400> SEQUENCE: 1

```
gatccaggaa aaacctggac agcatccggt gcagactttg cgtccaaggc tgaaacacc      60 ccatttgagg gccaggaatt cagcgctaag gtcacacaca ccgtgcttcg tggcaaggtg    120
acttgtgcag acggagttgc gcaagacgct taacgggtgg gtgcatagta tgcacgcgcc    180
gcattgcata taatgcaatg aattgaataa actacattga gggttatcaa ccagccaatt    240
tcttttaaaa agacagacac acgaaaggcg acaacagtca cc gtg agt aaa gac       294
                                                 Val Ser Lys Asp
                                                  1 acc acc acc tac cag gga gtc acc gag atc gga tcc gtt ccg gca tac      342
Thr Thr Thr Tyr Gln Gly Val Thr Glu Ile Gly Ser Val Pro Ala Tyr
 5              10                  15                  20 ctg gtt ctt gca gac gga cgt acc ttc acc gga ttt ggc ttt gga gct      390
Leu Val Leu Ala Asp Gly Arg Thr Phe Thr Gly Phe Gly Phe Gly Ala
                 25                  30                  35 atc ggc acc acc ctt ggt gag gca gtg ttc acc acc gcc atg acc ggt      438
Ile Gly Thr Thr Leu Gly Glu Ala Val Phe Thr Thr Ala Met Thr Gly
             40                  45                  50 tac caa gaa acc atg acc gat cct tcc tat cac cgc cag att gtt gtg      486
Tyr Gln Glu Thr Met Thr Asp Pro Ser Tyr His Arg Gln Ile Val Val
         55                  60                  65 gct acc gca cca cag atc ggt aac acc ggc tgg aac gat gag gac aac      534
Ala Thr Ala Pro Gln Ile Gly Asn Thr Gly Trp Asn Asp Glu Asp Asn
     70                  75                  80 gag tcc cgc gac ggc aag att tgg gtt gca ggc ctt gtt atc cgc gac      582
Glu Ser Arg Asp Gly Lys Ile Trp Val Ala Gly Leu Val Ile Arg Asp
 85                  90                  95                 100 ctc gca gca cgt gtg tcc aac tgg cgc gcc acc acc tcc ttg cag cag      630
Leu Ala Ala Arg Val Ser Asn Trp Arg Ala Thr Thr Ser Leu Gln Gln
                105                 110                 115 gaa atg gca gac caa ggc atc gtc ggc atc ggc gga atc gac acc cgc      678
Glu Met Ala Asp Gln Gly Ile Val Gly Ile Gly Gly Ile Asp Thr Arg
            120                 125                 130 gca ctg gtt cgc cac ctg cgc aac gaa ggt tcc atc gca gcg ggc atc      726
Ala Leu Val Arg His Leu Arg Asn Glu Gly Ser Ile Ala Ala Gly Ile
        135                 140                 145 ttc tcc ggc gct gac gca cag cgc cca gtt gaa gaa ctc gta gag atc      774
Phe Ser Gly Ala Asp Ala Gln Arg Pro Val Glu Glu Leu Val Glu Ile
    150                 155                 160 gtc aag aat cag cca gca atg acc ggc gca aac ctc tcc gtt gag gtc      822
Val Lys Asn Gln Pro Ala Met Thr Gly Ala Asn Leu Ser Val Glu Val
165                 170                 175                 180 tct gct gat gaa acc tac gtc atc gaa gct gag ggc gaa gag cgc cac      870
Ser Ala Asp Glu Thr Tyr Val Ile Glu Ala Glu Gly Glu Glu Arg His
                185                 190                 195
```

-continued

```
acc gtc gtg gcc tac gac ctg ggc att aag caa aac acc cca cgt cgt      918
Thr Val Val Ala Tyr Asp Leu Gly Ile Lys Gln Asn Thr Pro Arg Arg
            200                 205                 210 ttc tct gca cgc ggt gtt cgc acc gtc atc gtg cct gct gaa acc cca      966
Phe Ser Ala Arg Gly Val Arg Thr Val Ile Val Pro Ala Glu Thr Pro
        215                 220                 225 ttg gag gac atc aag cag tac aac cca tca ggc gtg ttt atc tcc aat     1014
Leu Glu Asp Ile Lys Gln Tyr Asn Pro Ser Gly Val Phe Ile Ser Asn
    230                 235                 240 ggc cct ggc gac cct gca gca gca gac gtc atg gtt gat atc gtc cgc     1062
Gly Pro Gly Asp Pro Ala Ala Ala Asp Val Met Val Asp Ile Val Arg
245                 250                 255                 260 gaa gtt ctg gaa gcc gac att cca ttc ttt ggc atc tgc ttc ggc aac     1110
Glu Val Leu Glu Ala Asp Ile Pro Phe Phe Gly Ile Cys Phe Gly Asn
                265                 270                 275 cag atc ctc ggc cgc gca ttc ggc atg gag acc tac aag ctg aag ttc     1158
Gln Ile Leu Gly Arg Ala Phe Gly Met Glu Thr Tyr Lys Leu Lys Phe
            280                 285                 290 ggc cac cgc ggc atc aac gtt cca gtg aag aac cac atc acc ggc aag     1206
Gly His Arg Gly Ile Asn Val Pro Val Lys Asn His Ile Thr Gly Lys
        295                 300                 305 atc gac atc acc gcc cag aac cac ggc ttc gca ctc aag ggt gaa gca     1254
Ile Asp Ile Thr Ala Gln Asn His Gly Phe Ala Leu Lys Gly Glu Ala
    310                 315                 320 ggc cag gaa ttc gag aca gat ttc ggc act gcg att gtc acc cac acc     1302
Gly Gln Glu Phe Glu Thr Asp Phe Gly Thr Ala Ile Val Thr His Thr
325                 330                 335                 340 tgc ctt aac gac ggc gtc gtt gaa ggt gtt gcg ctg aag tcc gga cgc     1350
Cys Leu Asn Asp Gly Val Val Glu Gly Val Ala Leu Lys Ser Gly Arg
                345                 350                 355 gca tac tcc gtt cag tac cac cca gag gcc gct gcc ggc cca aat gat     1398
Ala Tyr Ser Val Gln Tyr His Pro Glu Ala Ala Ala Gly Pro Asn Asp
            360                 365                 370 gca agc ccc ctg ttt gac cag ttt gtt gag ctg atg gat gca gac gct     1446
Ala Ser Pro Leu Phe Asp Gln Phe Val Glu Leu Met Asp Ala Asp Ala
        375                 380                 385 cag aag aaa ggc gca taaataac atg cca aag cgt tca gat att aac cac    1496
Gln Lys Lys Gly Ala           Met Pro Lys Arg Ser Asp Ile Asn His
    390                           395                 400 gtc ctc gtc atc ggt tcc ggc ccc atc gtc att ggc cag gca tgt gaa     1544
Val Leu Val Ile Gly Ser Gly Pro Ile Val Ile Gly Gln Ala Cys Glu
                405                 410                 415 ttc gac tac tcc ggc acc cag gct tgc cgc gtg ctg aag gaa gag gga     1592
Phe Asp Tyr Ser Gly Thr Gln Ala Cys Arg Val Leu Lys Glu Glu Gly
            420                 425                 430 ctg cgc gtc acc ctc atc aac tcc aac cca gca acg atc atg acc gac     1640
Leu Arg Val Thr Leu Ile Asn Ser Asn Pro Ala Thr Ile Met Thr Asp
435                 440                 445                 450 cca gaa atg gct gac cac acc tac gtg gag cca atc gag ccg gaa tac     1688
Pro Glu Met Ala Asp His Thr Tyr Val Glu Pro Ile Glu Pro Glu Tyr
                455                 460                 465 atc gac aag att ttc gct aag gag atc gag cag ggc cac cca atc gac     1736
Ile Asp Lys Ile Phe Ala Lys Glu Ile Glu Gln Gly His Pro Ile Asp
            470                 475                 480 gcc gtc ctg gca acc ctt ggt ggc cag act gca ctt aac gca gct atc     1784
Ala Val Leu Ala Thr Leu Gly Gly Gln Thr Ala Leu Asn Ala Ala Ile
        485                 490                 495 cag ctg gat cgc ctc ggc atc ctg gaa aag tac ggc gtt gaa ctc atc     1832
Gln Leu Asp Arg Leu Gly Ile Leu Glu Lys Tyr Gly Val Glu Leu Ile
```

-continued

| | | | | | | | | | | | | | |
|---|---|---|---|---|---|---|---|---|---|---|---|---|---|
| | | 500 | | | 505 | | | 510 | | | | | |
| ggt | gca | gac | atc | gat | gcc | att | gag | cgc | ggc | gaa | gat | cgc | cag | aag | ttc | 1880 |
| Gly | Ala | Asp | Ile | Asp | Ala | Ile | Glu | Arg | Gly | Glu | Asp | Arg | Gln | Lys | Phe | |
| 515 | | | | 520 | | | | | 525 | | | | | 530 | | | aag gat att gtc acc acc atc ggt ggc gaa tcc gcg cgt tcc cgc gtc   1928
Lys Asp Ile Val Thr Thr Ile Gly Gly Glu Ser Ala Arg Ser Arg Val
                535                 540                 545 tgc cac aac atg gac gaa gtc cat gag act gtc gca gaa ctt ggc ctt   1976
Cys His Asn Met Asp Glu Val His Glu Thr Val Ala Glu Leu Gly Leu
            550                 555                 560 cca gta gtc gtg cgt cca tcc ttc act atg ggt ggc ctg ggc tcc ggt   2024
Pro Val Val Val Arg Pro Ser Phe Thr Met Gly Gly Leu Gly Ser Gly
                565                 570                 575 ctt gca tac aac acc gaa gac ctt gag cgc atc gca ggt ggc gga ctt   2072
Leu Ala Tyr Asn Thr Glu Asp Leu Glu Arg Ile Ala Gly Gly Gly Leu
        580                 585                 590 gct gca tct cct gaa gca aac gtc ttg atc gaa gaa tcc atc ctt ggt   2120
Ala Ala Ser Pro Glu Ala Asn Val Leu Ile Glu Glu Ser Ile Leu Gly
595                 600                 605                 610 tgg aag gaa ttc gag ctc gag ctc atg cgc gat acc gca gac aac gtt   2168
Trp Lys Glu Phe Glu Leu Glu Leu Met Arg Asp Thr Ala Asp Asn Val
                615                 620                 625 gtg gtt atc tgc tcc att gaa aac gtc gac gca ctg ggc gtg cac acc   2216
Val Val Ile Cys Ser Ile Glu Asn Val Asp Ala Leu Gly Val His Thr
            630                 635                 640 ggc gac tct gtc acc gtg gca cct gcc ctg acc ctg act gac cgt gaa   2264
Gly Asp Ser Val Thr Val Ala Pro Ala Leu Thr Leu Thr Asp Arg Glu
                645                 650                 655 ttc cag aag atg cgc gat cag ggt atc gcc atc atc cgc gag gtc ggc   2312
Phe Gln Lys Met Arg Asp Gln Gly Ile Ala Ile Ile Arg Glu Val Gly
    660                 665                 670 gtg gac acc ggt gga tgt aac atc cag ttc gct atc aac cca gtt gat   2360
Val Asp Thr Gly Gly Cys Asn Ile Gln Phe Ala Ile Asn Pro Val Asp
675                 680                 685                 690 ggc cgc atc atc acc att gag atg aac cca cgt gtg tct cgt tcc tcc   2408
Gly Arg Ile Ile Thr Ile Glu Met Asn Pro Arg Val Ser Arg Ser Ser
                695                 700                 705 gcg ctg gca tcc aag gca acg ggc ttc cca att gcc aag atg gct gcc   2456
Ala Leu Ala Ser Lys Ala Thr Gly Phe Pro Ile Ala Lys Met Ala Ala
            710                 715                 720 aag ctg gct atc gga tac acc ctg gat gag atc acc aac gac atc act   2504
Lys Leu Ala Ile Gly Tyr Thr Leu Asp Glu Ile Thr Asn Asp Ile Thr
                725                 730                 735 ggt gaa acc cca gct gcg ttt gag ccc acc atc gac tac gtc gtg gtc   2552
Gly Glu Thr Pro Ala Ala Phe Glu Pro Thr Ile Asp Tyr Val Val Val
    740                 745                 750 aag gcc cca cgc ttt gct ttc gag aag ttt gtc ggc gct gat gac act   2600
Lys Ala Pro Arg Phe Ala Phe Glu Lys Phe Val Gly Ala Asp Asp Thr
755                 760                 765                 770 ttg acc acc acc atg aag tcc gtc ggt gag gtc atg tcc ctg ggc cgt   2648
Leu Thr Thr Thr Met Lys Ser Val Gly Glu Val Met Ser Leu Gly Arg
                775                 780                 785 aac tac att gca gca ctg aac aag gca ctg cgt tcc ctg gaa acc aag   2696
Asn Tyr Ile Ala Ala Leu Asn Lys Ala Leu Arg Ser Leu Glu Thr Lys
            790                 795                 800 cag cag ggt ttc tgg acc aag cct gat gag ttc ttc gca ggg gag cgc   2744
Gln Gln Gly Phe Trp Thr Lys Pro Asp Glu Phe Phe Ala Gly Glu Arg
    805                 810                 815 gct acc gat aag gca gct gtt ctg gaa gat ctc aag cgc cca acc gaa   2792

-continued

```
                Ala Thr Asp Lys Ala Ala Val Leu Glu Asp Leu Lys Arg Pro Thr Glu
                    820                 825                 830 ggc cgc ctc tac gac gtt gag ctg gca atg cgc ctt ggc gca agc gtg        2840
Gly Arg Leu Tyr Asp Val Glu Leu Ala Met Arg Leu Gly Ala Ser Val
835                 840                 845                 850 gaa gaa ctc tac gaa gca tct tct att gat cct tgg ttc ctc gcc gag        2888
Glu Glu Leu Tyr Glu Ala Ser Ser Ile Asp Pro Trp Phe Leu Ala Glu
                855                 860                 865 ctt gaa gct ctc gtg cag ttc cgc cag aag ctc gtt gac gca cca ttc        2936
Leu Glu Ala Leu Val Gln Phe Arg Gln Lys Leu Val Asp Ala Pro Phe
            870                 875                 880 ctc aac gaa gat ctc ctg cgc gaa gca aag ttc atg ggt ctg tcc gac        2984
Leu Asn Glu Asp Leu Leu Arg Glu Ala Lys Phe Met Gly Leu Ser Asp
        885                 890                 895 ctg cag atc gca gcc ctt cgc cca gag ttc gct ggc gaa gac ggc gta        3032
Leu Gln Ile Ala Ala Leu Arg Pro Glu Phe Ala Gly Glu Asp Gly Val
    900                 905                 910 cgc acc ttg cgt ctg tcc cta ggc atc cgc cca gta ttc aag act gtg        3080
Arg Thr Leu Arg Leu Ser Leu Gly Ile Arg Pro Val Phe Lys Thr Val
915                 920                 925                 930 gat acc tgt gca gca gag ttt gaa gct aag act ccg tac cac tac tcc        3128
Asp Thr Cys Ala Ala Glu Phe Glu Ala Lys Thr Pro Tyr His Tyr Ser
                935                 940                 945 gca tac gag ctg gat cca gca gct gag tct gag gtc gca cca cag act        3176
Ala Tyr Glu Leu Asp Pro Ala Ala Glu Ser Glu Val Ala Pro Gln Thr
            950                 955                 960 gag cgt gaa aag gtc ctg atc ttg ggc tcc ggt cca aac cgc atc ggc        3224
Glu Arg Glu Lys Val Leu Ile Leu Gly Ser Gly Pro Asn Arg Ile Gly
        965                 970                 975 cag ggc atc gag ttc gac tat tcc tgt gtt cac gca gct ctt gag ctc        3272
Gln Gly Ile Glu Phe Asp Tyr Ser Cys Val His Ala Ala Leu Glu Leu
    980                 985                 990 tcc cgc gtc ggc tac gaa  act gtc atg gtc aac  tgc aac cca gag         3317
Ser Arg Val Gly Tyr Glu  Thr Val Met Val Asn  Cys Asn Pro Glu
995                 1000                 1005 acc gtg tcc acc gac tac  gac acc gct gac cgc  ctg tac ttc gag         3362
Thr Val Ser Thr Asp Tyr  Asp Thr Ala Asp Arg  Leu Tyr Phe Glu
1010                1015                 1020 cca ctg acc ttc gaa gac  gtc atg gag gtc tac  cac gct gag gcg         3407
Pro Leu Thr Phe Glu Asp  Val Met Glu Val Tyr  His Ala Glu Ala
1025                1030                 1035 cag tcc ggc acc gtc gca  ggt gtt atc gtc cag  ctt ggt ggc cag         3452
Gln Ser Gly Thr Val Ala  Gly Val Ile Val Gln  Leu Gly Gly Gln
1040                1045                 1050 act cct ctg ggc ttg gca  gat cgt ttg aag aag  gct ggc gtc cct         3497
Thr Pro Leu Gly Leu Ala  Asp Arg Leu Lys Lys  Ala Gly Val Pro
1055                1060                 1065 gtc att ggt acc tcc cca  gag gca atc gac atg  gct gag gac cgt         3542
Val Ile Gly Thr Ser Pro  Glu Ala Ile Asp Met  Ala Glu Asp Arg
1070                1075                 1080 ggc gag ttc ggt gca ctg  ctg aac cgc gag cag  ctt cct gct cca         3587
Gly Glu Phe Gly Ala Leu  Leu Asn Arg Glu Gln  Leu Pro Ala Pro
1085                1090                 1095 gca ttc ggc acc gca acc  tct ttc gaa gag gct  cgc aca gta gcc         3632
Ala Phe Gly Thr Ala Thr  Ser Phe Glu Glu Ala  Arg Thr Val Ala
1100                1105                 1110 gat gag atc agc tac cca  gtg ctg gtt cgc cct  tcc tac gtc ttg         3677
Asp Glu Ile Ser Tyr Pro  Val Leu Val Arg Pro  Ser Tyr Val Leu
1115                1120                 1125
```

-continued

| | | | | | | | | | | | | | | |
|---|---|---|---|---|---|---|---|---|---|---|---|---|---|---|
| ggt | ggc | cgt | ggc | atg | gag | att | gtc | tac | gat | gag | gct | tcc | ctc | gag | 3722 |
| Gly | Gly | Arg | Gly | Met | Glu | Ile | Val | Tyr | Asp | Glu | Ala | Ser | Leu | Glu | |
| 1130 | | | | 1135 | | | | | 1140 | | | | | | |
| gat | tac | atc | aac | cgc | gca | act | gag | ttg | tct | tct | gac | cac | cca | gtg | 3767 |
| Asp | Tyr | Ile | Asn | Arg | Ala | Thr | Glu | Leu | Ser | Ser | Asp | His | Pro | Val | |
| 1145 | | | | 1150 | | | | | 1155 | | | | | | |
| ctg | gtt | gac | cgc | ttc | ctg | gac | aac | gct | att | gag | atc | gac | gtc | gac | 3812 |
| Leu | Val | Asp | Arg | Phe | Leu | Asp | Asn | Ala | Ile | Glu | Ile | Asp | Val | Asp | |
| 1160 | | | | 1165 | | | | | 1170 | | | | | | |
| gca | ctg | tgc | gac | ggc | gac | gaa | gtc | tac | ctg | gcg | ggc | gtc | atg | gaa | 3857 |
| Ala | Leu | Cys | Asp | Gly | Asp | Glu | Val | Tyr | Leu | Ala | Gly | Val | Met | Glu | |
| 1175 | | | | 1180 | | | | | 1185 | | | | | | |
| cac | atc | gag | gaa | gcc | ggc | att | cac | tcc | ggt | gac | tcc | gca | tgt | gca | 3902 |
| His | Ile | Glu | Glu | Ala | Gly | Ile | His | Ser | Gly | Asp | Ser | Ala | Cys | Ala | |
| 1190 | | | | 1195 | | | | | 1200 | | | | | | |
| ctt | cct | cca | atg | act | ttg | ggc | gca | cag | gac | atc | gag | aag | gtc | cgc | 3947 |
| Leu | Pro | Pro | Met | Thr | Leu | Gly | Ala | Gln | Asp | Ile | Glu | Lys | Val | Arg | |
| 1205 | | | | 1210 | | | | | 1215 | | | | | | |
| gaa | gca | acc | aag | aag | ctg | gct | ctg | ggc | atc | ggc | gta | cag | ggc | ctg | 3992 |
| Glu | Ala | Thr | Lys | Lys | Leu | Ala | Leu | Gly | Ile | Gly | Val | Gln | Gly | Leu | |
| 1220 | | | | 1225 | | | | | 1230 | | | | | | |
| atg | aac | gtc | cag | tac | gca | ctc | aag | gac | gac | atc | ctc | tac | gtc | atc | 4037 |
| Met | Asn | Val | Gln | Tyr | Ala | Leu | Lys | Asp | Asp | Ile | Leu | Tyr | Val | Ile | |
| 1235 | | | | 1240 | | | | | 1245 | | | | | | |
| gag | gca | aac | cca | cgt | gca | tcc | cgc | acc | gtg | ccg | ttc | gtc | tcc | aag | 4082 |
| Glu | Ala | Asn | Pro | Arg | Ala | Ser | Arg | Thr | Val | Pro | Phe | Val | Ser | Lys | |
| 1250 | | | | 1255 | | | | | 1260 | | | | | | |
| gca | acg | ggc | gtc | aac | ctg | gcc | aag | gca | gca | tcc | cgt | atc | gca | gtg | 4127 |
| Ala | Thr | Gly | Val | Asn | Leu | Ala | Lys | Ala | Ala | Ser | Arg | Ile | Ala | Val | |
| 1265 | | | | 1270 | | | | | 1275 | | | | | | |
| ggc | gcc | acc | atc | aag | gat | ctc | caa | gat | gag | ggc | atg | att | cct | acc | 4172 |
| Gly | Ala | Thr | Ile | Lys | Asp | Leu | Gln | Asp | Glu | Gly | Met | Ile | Pro | Thr | |
| 1280 | | | | 1285 | | | | | 1290 | | | | | | |
| gag | tac | gac | ggc | ggc | tcc | ttg | cca | ctg | gac | gct | cca | atc | gct | gtg | 4217 |
| Glu | Tyr | Asp | Gly | Gly | Ser | Leu | Pro | Leu | Asp | Ala | Pro | Ile | Ala | Val | |
| 1295 | | | | 1300 | | | | | 1305 | | | | | | |
| aag | gaa | gca | gtg | ttg | ccg | ttc | aac | cgc | ttc | cgt | cgc | cca | gat | gga | 4262 |
| Lys | Glu | Ala | Val | Leu | Pro | Phe | Asn | Arg | Phe | Arg | Arg | Pro | Asp | Gly | |
| 1310 | | | | 1315 | | | | | 1320 | | | | | | |
| aag | acc | ctg | gac | acc | ctg | ctt | tcc | cca | gag | atg | aag | tcc | act | ggc | 4307 |
| Lys | Thr | Leu | Asp | Thr | Leu | Leu | Ser | Pro | Glu | Met | Lys | Ser | Thr | Gly | |
| 1325 | | | | 1330 | | | | | 1335 | | | | | | |
| gag | gtc | atg | ggc | ttg | gcc | aac | aac | ttc | ggc | gct | gca | tat | gca | aag | 4352 |
| Glu | Val | Met | Gly | Leu | Ala | Asn | Asn | Phe | Gly | Ala | Ala | Tyr | Ala | Lys | |
| 1340 | | | | 1345 | | | | | 1350 | | | | | | |
| gct | gaa | gct | ggc | gcg | ttt | ggt | gca | ttg | cca | acc | gaa | ggc | acc | gtc | 4397 |
| Ala | Glu | Ala | Gly | Ala | Phe | Gly | Ala | Leu | Pro | Thr | Glu | Gly | Thr | Val | |
| 1355 | | | | 1360 | | | | | 1365 | | | | | | |
| ttc | gtg | acc | gtg | gct | aac | cgc | gac | aag | cgc | acc | ctg | atc | ctg | cca | 4442 |
| Phe | Val | Thr | Val | Ala | Asn | Arg | Asp | Lys | Arg | Thr | Leu | Ile | Leu | Pro | |
| 1370 | | | | 1375 | | | | | 1380 | | | | | | |
| atc | cag | cgc | ctg | gcg | tcg | atg | ggc | tac | aag | atc | ctc | gcc | acc | gaa | 4487 |
| Ile | Gln | Arg | Leu | Ala | Ser | Met | Gly | Tyr | Lys | Ile | Leu | Ala | Thr | Glu | |
| 1385 | | | | 1390 | | | | | 1395 | | | | | | |
| ggc | acc | gca | ggc | atg | ctg | cgc | cgc | aac | ggc | att | gat | tgt | gaa | gtt | 4532 |
| Gly | Thr | Ala | Gly | Met | Leu | Arg | Arg | Asn | Gly | Ile | Asp | Cys | Glu | Val | |
| 1400 | | | | 1405 | | | | | 1410 | | | | | | |
| gtg | ctc | aag | gct | tcc | gac | atc | cgc | gaa | ggt | gta | gag | ggc | aag | tcc | 4577 |
| Val | Leu | Lys | Ala | Ser | Asp | Ile | Arg | Glu | Gly | Val | Glu | Gly | Lys | Ser | |
| 1415 | | | | 1420 | | | | | 1425 | | | | | | |

```
atc gtg gat cgt atc cgc gaa ggc gaa gtt gac ctc atc ctc aac    4622
Ile Val Asp Arg Ile Arg Glu Gly Glu Val Asp Leu Ile Leu Asn
1430            1435                1440 acc cca gct ggt tct gct ggc gct cgc cac gat ggc tac gat atc    4667
Thr Pro Ala Gly Ser Ala Gly Ala Arg His Asp Gly Tyr Asp Ile
1445            1450                1455 cgc gca gca gca gtg acc gtg ggt gtt cca ctg atc acc act gtc    4712
Arg Ala Ala Ala Val Thr Val Gly Val Pro Leu Ile Thr Thr Val
1460            1465                1470 cag ggt gtc acc gca gct gtc cag ggc att gag gcc ctg cgt gag    4757
Gln Gly Val Thr Ala Ala Val Gln Gly Ile Glu Ala Leu Arg Glu
1475            1480                1485 ggc gtt gtc agc gtc cgc gcg ctg cag gaa ctc gac cac gca gtc    4802
Gly Val Val Ser Val Arg Ala Leu Gln Glu Leu Asp His Ala Val
1490            1495                1500 aag gct taagccctat gacattcggc gagaagctt                        4837
Lys Ala
1505

<210> SEQ ID NO 2
<211> LENGTH: 393
<212> TYPE: PRT
<213> ORGANISM: Brevibacterium lactofermentum

<400> SEQUENCE: 2

Val Ser Lys Asp Thr Thr Thr Tyr Gln Gly Val Thr Glu Ile Gly Ser
1               5                   10                  15

Val Pro Ala Tyr Leu Val Leu Ala Asp Gly Arg Thr Phe Thr Gly Phe
                20                  25                  30

Gly Phe Gly Ala Ile Gly Thr Thr Leu Gly Glu Ala Val Phe Thr Thr
            35                  40                  45

Ala Met Thr Gly Tyr Gln Glu Thr Met Thr Asp Pro Ser Tyr His Arg
        50                  55                  60

Gln Ile Val Val Ala Thr Ala Pro Gln Ile Gly Asn Thr Gly Trp Asn
65                  70                  75                  80

Asp Glu Asp Asn Glu Ser Arg Asp Gly Lys Ile Trp Val Ala Gly Leu
                85                  90                  95

Val Ile Arg Asp Leu Ala Ala Arg Val Ser Asn Trp Arg Ala Thr Thr
            100                 105                 110

Ser Leu Gln Gln Glu Met Ala Asp Gln Gly Ile Val Gly Ile Gly Gly
        115                 120                 125

Ile Asp Thr Arg Ala Leu Val Arg His Leu Arg Asn Glu Gly Ser Ile
    130                 135                 140

Ala Ala Gly Ile Phe Ser Gly Ala Asp Ala Gln Arg Pro Val Glu Glu
145                 150                 155                 160

Leu Val Glu Ile Val Lys Asn Gln Pro Ala Met Thr Gly Ala Asn Leu
                165                 170                 175

Ser Val Glu Val Ser Ala Asp Glu Thr Tyr Val Ile Glu Ala Glu Gly
            180                 185                 190

Glu Glu Arg His Thr Val Val Ala Tyr Asp Leu Gly Ile Lys Gln Asn
        195                 200                 205

Thr Pro Arg Arg Phe Ser Ala Arg Gly Val Arg Thr Val Ile Val Pro
    210                 215                 220

Ala Glu Thr Pro Leu Glu Asp Ile Lys Gln Tyr Asn Pro Ser Gly Val
225                 230                 235                 240

Phe Ile Ser Asn Gly Pro Gly Asp Pro Ala Ala Ala Asp Val Met Val
```

```
                245                 250                 255
Asp Ile Val Arg Glu Val Leu Glu Ala Asp Ile Pro Phe Phe Gly Ile
            260                 265                 270
Cys Phe Gly Asn Gln Ile Leu Gly Arg Ala Phe Gly Met Glu Thr Tyr
        275                 280                 285
Lys Leu Lys Phe Gly His Arg Gly Ile Asn Val Pro Val Lys Asn His
    290                 295                 300
Ile Thr Gly Lys Ile Asp Ile Thr Ala Gln Asn His Gly Phe Ala Leu
305                 310                 315                 320
Lys Gly Glu Ala Gly Gln Glu Phe Glu Thr Asp Phe Gly Thr Ala Ile
                325                 330                 335
Val Thr His Thr Cys Leu Asn Asp Gly Val Val Glu Gly Val Ala Leu
            340                 345                 350
Lys Ser Gly Arg Ala Tyr Ser Val Gln Tyr His Pro Glu Ala Ala Ala
        355                 360                 365
Gly Pro Asn Asp Ala Ser Pro Leu Phe Asp Gln Phe Val Glu Leu Met
    370                 375                 380
Asp Ala Asp Ala Gln Lys Lys Gly Ala
385                 390
```

<210> SEQ ID NO 3
<211> LENGTH: 1113
<212> TYPE: PRT
<213> ORGANISM: Brevibacterium lactofermentum

<400> SEQUENCE: 3

```
Met Pro Lys Arg Ser Asp Ile Asn His Val Leu Val Ile Gly Ser Gly
1               5                   10                  15
Pro Ile Val Ile Gly Gln Ala Cys Glu Phe Asp Tyr Ser Gly Thr Gln
                20                  25                  30
Ala Cys Arg Val Leu Lys Glu Glu Gly Leu Arg Val Thr Leu Ile Asn
            35                  40                  45
Ser Asn Pro Ala Thr Ile Met Thr Asp Pro Glu Met Ala Asp His Thr
        50                  55                  60
Tyr Val Glu Pro Ile Glu Pro Glu Tyr Ile Asp Lys Ile Phe Ala Lys
65                  70                  75                  80
Glu Ile Glu Gln Gly His Pro Ile Asp Ala Val Leu Ala Thr Leu Gly
                85                  90                  95
Gly Gln Thr Ala Leu Asn Ala Ala Ile Gln Leu Asp Arg Leu Gly Ile
            100                 105                 110
Leu Glu Lys Tyr Gly Val Glu Leu Ile Gly Ala Asp Ile Asp Ala Ile
        115                 120                 125
Glu Arg Gly Glu Asp Arg Gln Lys Phe Lys Asp Ile Val Thr Thr Ile
    130                 135                 140
Gly Gly Glu Ser Ala Arg Ser Arg Val Cys His Asn Met Asp Glu Val
145                 150                 155                 160
His Glu Thr Val Ala Glu Leu Gly Leu Pro Val Val Arg Pro Ser
                165                 170                 175
Phe Thr Met Gly Gly Leu Gly Ser Gly Leu Ala Tyr Asn Thr Glu Asp
            180                 185                 190
Leu Glu Arg Ile Ala Gly Gly Leu Ala Ala Ser Pro Glu Ala Asn
        195                 200                 205
Val Leu Ile Glu Glu Ser Ile Leu Gly Trp Lys Glu Phe Glu Leu Glu
    210                 215                 220
```

-continued

```
Leu Met Arg Asp Thr Ala Asp Asn Val Val Ile Cys Ser Ile Glu
225                 230                 235                 240

Asn Val Asp Ala Leu Gly Val His Thr Gly Asp Ser Val Thr Val Ala
            245                 250                 255

Pro Ala Leu Thr Leu Thr Asp Arg Glu Phe Gln Lys Met Arg Asp Gln
            260                 265                 270

Gly Ile Ala Ile Ile Arg Glu Val Gly Val Asp Thr Gly Gly Cys Asn
            275                 280                 285

Ile Gln Phe Ala Ile Asn Pro Val Asp Gly Arg Ile Ile Thr Ile Glu
            290                 295                 300

Met Asn Pro Arg Val Ser Arg Ser Ser Ala Leu Ala Ser Lys Ala Thr
305                 310                 315                 320

Gly Phe Pro Ile Ala Lys Met Ala Ala Lys Leu Ala Ile Gly Tyr Thr
                325                 330                 335

Leu Asp Glu Ile Thr Asn Asp Ile Thr Gly Glu Thr Pro Ala Ala Phe
                340                 345                 350

Glu Pro Thr Ile Asp Tyr Val Val Lys Ala Pro Arg Phe Ala Phe
                355                 360                 365

Glu Lys Phe Val Gly Ala Asp Asp Thr Leu Thr Thr Met Lys Ser
370                 375                 380

Val Gly Glu Val Met Ser Leu Gly Arg Asn Tyr Ile Ala Ala Leu Asn
385                 390                 395                 400

Lys Ala Leu Arg Ser Leu Glu Thr Lys Gln Gln Gly Phe Trp Thr Lys
                405                 410                 415

Pro Asp Glu Phe Phe Ala Gly Glu Arg Ala Thr Asp Lys Ala Ala Val
                420                 425                 430

Leu Glu Asp Leu Lys Arg Pro Thr Glu Gly Arg Leu Tyr Asp Val Glu
                435                 440                 445

Leu Ala Met Arg Leu Gly Ala Ser Val Glu Glu Leu Tyr Glu Ala Ser
450                 455                 460

Ser Ile Asp Pro Trp Phe Leu Ala Glu Leu Glu Ala Leu Val Gln Phe
465                 470                 475                 480

Arg Gln Lys Leu Val Asp Ala Pro Phe Leu Asn Glu Asp Leu Leu Arg
                485                 490                 495

Glu Ala Lys Phe Met Gly Leu Ser Asp Leu Gln Ile Ala Ala Leu Arg
                500                 505                 510

Pro Glu Phe Ala Gly Glu Asp Gly Val Arg Thr Leu Arg Leu Ser Leu
                515                 520                 525

Gly Ile Arg Pro Val Phe Lys Thr Val Asp Thr Cys Ala Ala Glu Phe
530                 535                 540

Glu Ala Lys Thr Pro Tyr His Tyr Ser Ala Tyr Glu Leu Asp Pro Ala
545                 550                 555                 560

Ala Glu Ser Glu Val Ala Pro Gln Thr Glu Arg Glu Lys Val Leu Ile
                565                 570                 575

Leu Gly Ser Gly Pro Asn Arg Ile Gly Gln Gly Ile Glu Phe Asp Tyr
                580                 585                 590

Ser Cys Val His Ala Ala Leu Glu Leu Ser Arg Val Gly Tyr Glu Thr
                595                 600                 605

Val Met Val Asn Cys Asn Pro Glu Thr Val Ser Thr Asp Tyr Asp Thr
610                 615                 620

Ala Asp Arg Leu Tyr Phe Glu Pro Leu Thr Phe Glu Asp Val Met Glu
625                 630                 635                 640

Val Tyr His Ala Glu Ala Gln Ser Gly Thr Val Ala Gly Val Ile Val
```

-continued

```
            645                 650                 655
Gln Leu Gly Gly Gln Thr Pro Leu Gly Leu Ala Asp Arg Leu Lys Lys
                660                 665                 670
Ala Gly Val Pro Val Ile Gly Thr Ser Pro Glu Ala Ile Asp Met Ala
                675                 680                 685
Glu Asp Arg Gly Glu Phe Gly Ala Leu Leu Asn Arg Glu Gln Leu Pro
        690                 695                 700
Ala Pro Ala Phe Gly Thr Ala Thr Ser Phe Glu Glu Ala Arg Thr Val
705                 710                 715                 720
Ala Asp Glu Ile Ser Tyr Pro Val Leu Val Arg Pro Ser Tyr Val Leu
                725                 730                 735
Gly Gly Arg Gly Met Glu Ile Val Tyr Asp Glu Ala Ser Leu Glu Asp
                740                 745                 750
Tyr Ile Asn Arg Ala Thr Glu Leu Ser Ser Asp His Pro Val Leu Val
                755                 760                 765
Asp Arg Phe Leu Asp Asn Ala Ile Glu Ile Asp Val Asp Ala Leu Cys
770                 775                 780
Asp Gly Asp Glu Val Tyr Leu Ala Gly Val Met Glu His Ile Glu Glu
785                 790                 795                 800
Ala Gly Ile His Ser Gly Asp Ser Ala Cys Ala Leu Pro Pro Met Thr
                805                 810                 815
Leu Gly Ala Gln Asp Ile Glu Lys Val Arg Glu Ala Thr Lys Lys Leu
                820                 825                 830
Ala Leu Gly Ile Gly Val Gln Gly Leu Met Asn Val Gln Tyr Ala Leu
                835                 840                 845
Lys Asp Asp Ile Leu Tyr Val Ile Glu Ala Asn Pro Arg Ala Ser Arg
850                 855                 860
Thr Val Pro Phe Val Ser Lys Ala Thr Gly Val Asn Leu Ala Lys Ala
865                 870                 875                 880
Ala Ser Arg Ile Ala Val Gly Ala Thr Ile Lys Asp Leu Gln Asp Glu
                885                 890                 895
Gly Met Ile Pro Thr Glu Tyr Asp Gly Gly Ser Leu Pro Leu Asp Ala
                900                 905                 910
Pro Ile Ala Val Lys Glu Ala Val Leu Pro Phe Asn Arg Phe Arg Arg
        915                 920                 925
Pro Asp Gly Lys Thr Leu Asp Thr Leu Leu Ser Pro Glu Met Lys Ser
        930                 935                 940
Thr Gly Glu Val Met Gly Leu Ala Asn Asn Phe Gly Ala Ala Tyr Ala
945                 950                 955                 960
Lys Ala Glu Ala Gly Ala Phe Gly Ala Leu Pro Thr Glu Gly Thr Val
                965                 970                 975
Phe Val Thr Val Ala Asn Arg Asp Lys Arg Thr Leu Ile Leu Pro Ile
                980                 985                 990
Gln Arg Leu Ala Ser Met Gly Tyr Lys Ile Leu Ala Thr Glu Gly Thr
        995                 1000                1005
Ala Gly Met Leu Arg Arg Asn Gly Ile Asp Cys Glu Val Val Leu
        1010                1015                1020
Lys Ala Ser Asp Ile Arg Glu Gly Val Glu Gly Lys Ser Ile Val
        1025                1030                1035
Asp Arg Ile Arg Glu Gly Glu Val Asp Leu Ile Leu Asn Thr Pro
        1040                1045                1050
Ala Gly Ser Ala Gly Ala Arg His Asp Gly Tyr Asp Ile Arg Ala
        1055                1060                1065
```

-continued

```
Ala Ala Val Thr Val Gly Val Pro Leu Ile Thr Thr Val Gln Gly
        1070            1075            1080

Val Thr Ala Ala Val Gln Gly Ile Glu Ala Leu Arg Glu Gly Val
    1085            1090            1095

Val Ser Val Arg Ala Leu Gln Glu Leu Asp His Ala Val Lys Ala
    1100            1105            1110

<210> SEQ ID NO 4
<211> LENGTH: 32
<212> TYPE: DNA
<213> ORGANISM: Artificial Sequence
<220> FEATURE:
<223> OTHER INFORMATION: synthetic DNA

<400> SEQUENCE: 4
cccgttaact gcttgaaacc caggacaata ac                              32

<210> SEQ ID NO 5
<211> LENGTH: 30
<212> TYPE: DNA
<213> ORGANISM: Artificial Sequence
<220> FEATURE:
<223> OTHER INFORMATION: synthetic DNA

<400> SEQUENCE: 5
cccgttaaca tgtacttcag aaaagattag                                 30

<210> SEQ ID NO 6
<211> LENGTH: 26
<212> TYPE: DNA
<213> ORGANISM: Artificial Sequence
<220> FEATURE:
<223> OTHER INFORMATION: synthetic DNA

<400> SEQUENCE: 6
gatatctacg tgccgatcaa cgtctc                                     26

<210> SEQ ID NO 7
<211> LENGTH: 25
<212> TYPE: DNA
<213> ORGANISM: Artificial Sequence
<220> FEATURE:
<223> OTHER INFORMATION: synthetic DNA

<400> SEQUENCE: 7
aggccttttt ttaaggcagt tattg                                      25
```

US 6,908,754 B2

CARBAMOYL-PHOSPHATE SYNTHETASE GENE OF CORYNEFORM BACTERIA AND METHOD FOR PRODUCING L-ARGININE

CROSS-REFERENCE TO RELATED APPLICATIONS

The present application is a division of application Ser. No. 09/494,359 filed Jan. 31, 2000 (now abandoned).

BACKGROUND OF THE INVENTION

1. Field of the Invention

The present invention relates to carbamoyl-phosphate synthetase of coryneform bacteria, and a gene therefor. The gene can be utilized for production of carbamoyl-phosphate synthetase and subunits thereof, breeding of L-arginine-producing bacteria and nucleic acid-producing bacteria and so forth.

2. Description of the Related Art

Carbamoyl-phosphate synthetase is an enzyme that catalyzes the reactions producing carbamoyl phosphate from carbonic acid, ATP and glutamine. Carbamoyl phosphate produced by these reactions serves as a source of carbamoyl group required for the reaction producing citrulline from ornithine in the L-arginine biosynthetic pathway. Furthermore, carbamoyl aspartate produced from aspartic acid and carbamoyl phosphate is one of the intermediates of the pyrimidine biosynthesis system including uridine 5'-monophosphate.

Carbamoyl-phosphate synthetase consists of two subunits, and it has been known for bacteria belonging to the genus Escherichia or Bacillus that those subunits are encoded by carA and carB genes.

However, as for coryneform bacteria, there have been no findings about the carbamoyl-phosphate synthetase activity and enzymes therefor, and any genes therefor have not been elucidated.

Incidentally, it has been reported that when a transformant of *Escherichia coli* to which introduced a plasmid harboring the genes carA, carB, argI and arg box was cultured in the medium added with glutamine which is substrate of carbamoyl-phosphate synthetase, the concentration of intracellular L-arginine was the same as that of a control strain to which only the vector was introduced. However, when the transformant was cultured in a medium added with glutamine accompanied with ornithine which is a substrate of ArgI together with carbamoyl phosphate, the concentration of intracellular L-arginine was higher than that of the control strain (Malamy M. et al., *Applied Environmental Microbiology*, 63(1), 33 (1997)). From these result, it was suggested that the rate-determining step of synthesis of L-arginine is supply of ornithine.

There was thought to be a possibility that the rate-determining step of supply of ornithine is N-acetylglutamine synthetase (ArgA). ArgA suffers feedback inhibition by the final product, L-arginine, in the biosynthesis pathway of *Escherichia coli*.

As for the strain in which argA gene coding for feedback inhibition-desensitized ArgA was amplified by plasmid, the concentration of intracellular L-arginine was increased even in a medium added with only glutamine as well as in a medium added with both glutamine and ornithine. However, farther increase of concentration of intracellular L-arginine was not observed in the case that the strain was cultured with addition of glutamine, or glutamine and ornithin, also in the case that the both of carA and carB genes were further amplified in the strain (Malamy M. et al., *Applied Environmental Microbiology*, 64(5), 1805 (1998)).

On the other hand, any attempts have not been reported to enhance L-arginine productibity of microorganisms by utilizing a gene coding for carbamoyl-phosphate synthetase derived from coryneform bacterium.

SUMMARY OF THE INVENTION

An object of the present invention is to provide carbamoyl-phosphate synthetase of coryneform bacteria, a gene coding for it, and a method for producing L-arginine with a microorganism utilizing the gene.

The inventors of the present invention eagerly studied in order to achieve the aforementioned object. As a result, the inventors successfully obtained a DNA fragment containing the carA gene and the carB gene from a wild strain of *Brevibacterium lactofermentum* by utilizing a carB-deficient strain of *Escherichia coli,* and thus accomplished the present invention.

That is, the present invention provides the followings.

(1) A DNA fragment which encodes a polypeptide defined in the following (A) or (B):

(A) a polypeptide which has an amino acid sequence comprises at least the amino acid numbers 50 to 393 of the amino acid sequence of SEQ ID NO: 2, (B) a polypeptide which has an amino acid sequence comprises at least the amino acid numbers 50 to 393 of the amino acid sequence of SEQ ID NO: 2 including substitution, deletion, insertion, addition, or inversion of one or several amino acids, and can constitute a protein having a carbamoyl-phosphate synthetase activity with a large subunit of carbamoyl-phosphate synthetase comprising the amino acid sequence of SEQ ID NO: 3.

(2) A DNA fragment which encodes a polypeptide defined in the following (C) or (D):

(C) a polypeptide which comprises the amino acid sequence of SEQ ID NO: 3, (D) a polypeptide which comprises the amino acid sequence of SEQ ID NO: 3 including substitution, deletion, insertion, addition, or inversion of one or several amino acids, and can constitute a protein having a carbamoyl-phosphate synthetase activity with a small subunit of carbamoyl-phosphate synthetase having an amino acid sequence comprises at least the amino acid numbers 50 to 393 of the amino acid sequence of SEQ ID NO: 2.

(3) A DNA fragment encoding a polypeptide which comprises the amino acid sequence of SEQ ID NO: 3 including substitution, deletion, insertion, addition, or inversion of one or several amino acids, and can constitute a protein having a carbamoyl-phosphate synthetase activity.

(4) A DNA fragment which encodes a polypeptide defined in the following (a) or (b), and a polypeptide defined in the following (c) or (d):

(a) a polypeptide which has an amino acid sequence comprising at least the amino acid numbers 50 to 393 in SEQ ID NO: 2, (b) a polypeptide which has an amino acid sequence comprising at least the amino acid numbers 50 to 393 in SEQ ID NO: 2 including substitution, deletion, insertion, addition, or inversion of one or several amino acids, and can constitute a protein having a carbamoyl-phosphate synthetase activity with a large subunit of carbamoyl-phosphate synthetase comprising the amino acid sequence of SEQ ID NO: 3, (c) a polypeptide which comprises the amino acid sequence of SEQ ID NO: 3, (d) a polypeptide which comprises the amino acid sequence of SEQ ID NO: 3 including substitution, deletion, insertion, addition, or inversion of one or several amino acids, and can constitute a protein having a carbamoyl-phosphate synthetase activity with a small subunit of carbamoyl-phosphate synthetase having an amino acid sequence comprising the amino acid numbers 50 to 393 in SEQ ID NO: 2.

(5) The DNA fragment according to (1), which has a nucleotide sequence comprising at least the nucleotide numbers 430 to 1461 in the nucleotide sequence of SEQ ID NO: 1.

(6) The DNA fragment according to (2), which has a nucleotide sequence comprising at least the nucleotide numbers 1756 to 4809 in the nucleotide sequence of SEQ ID NO: 1.

(7) The DNA fragment according to (3), which has a nucleotide sequence comprising at least the nucleotide numbers 430 to 4809 in the nucleotide sequence of SEQ ID NO: 1.

(8) A protein which comprises a polypeptide defined in the following (a) or (b), and a polypeptide defined in the following (c) or (d):

(a) a polypeptide which has an amino acid sequence comprising at least the amino acid numbers 50 to 393 in SEQ ID NO: 2, (b) a polypeptide which has an amino acid sequence comprising at least the amino acid numbers 50 to 393 in SEQ ID NO: 2 including substitution, deletion, insertion, addition, or inversion of one or several amino acids, and can constitute a protein having a carbamoyl-phosphate synthetase activity with a large subunit of carbamoyl-phosphate synthetase comprising the amino acid sequence of SEQ ID NO: 3, (c) a polypeptide which comprises the amino acid sequence of SEQ ID NO: 3, (d) a polypeptide which comprises the amino acid sequence of SEQ ID NO: 3 including substitution, deletion, insertion, addition, or inversion of one or several amino acids, and can constitute a protein having a carbamoyl-phosphate synthetase activity with a small subunit of carbamoyl-phosphate synthetase having an amino acid sequence comprising at least the amino acid numbers 50 to 393 in SEQ ID NO: 2.

(9) A coryneform bacterium which is transformed with a DNA fragment according to any one of (1) to (7).

(10) A microorganism which has enhanced intracellular carbamoyl-phosphate synthetase activity, and has L-arginine productivity.

(11) The microorganism according to (10), wherein the enhanced intracellular carbamoyl-phosphate synthetase activity is obtained by increasing copy number of DNA encoding carbamoyl-phosphate synthetase of the microorganism, or by modifying an expression regulation sequence so that expression of the gene encoding carbamoyl-phosphate synthetase in the cell should be enhanced.

(12) The microorganism according to (11), wherein the DNA is a DNA fragment according to any one of (1) to (7).

(13) The microorganism according to (12), which is a coryneform bacterium.

(14) A method for producing of L-arginine, comprising the steps of culturing a coryneform bacterium according to any one of (10) to (13) in a medium to produce and accumulate L-arginine in the medium, and collecting the L-arginine from the medium.

The present invention provides genes coding for the subunits that constitute carbamoyl-phosphate synthetase. The gene can be utilized for production of carbamoyl-phosphate synthetase and subunits thereof, breeding of L-arginine-producing bacteria and nucleic acid-producing bacteria and so forth. Aditionally, L-arginine can be produced efficiently according to the present invention.

DETAIL DESCRIPTION OF THE INVENTION

Figure 1:
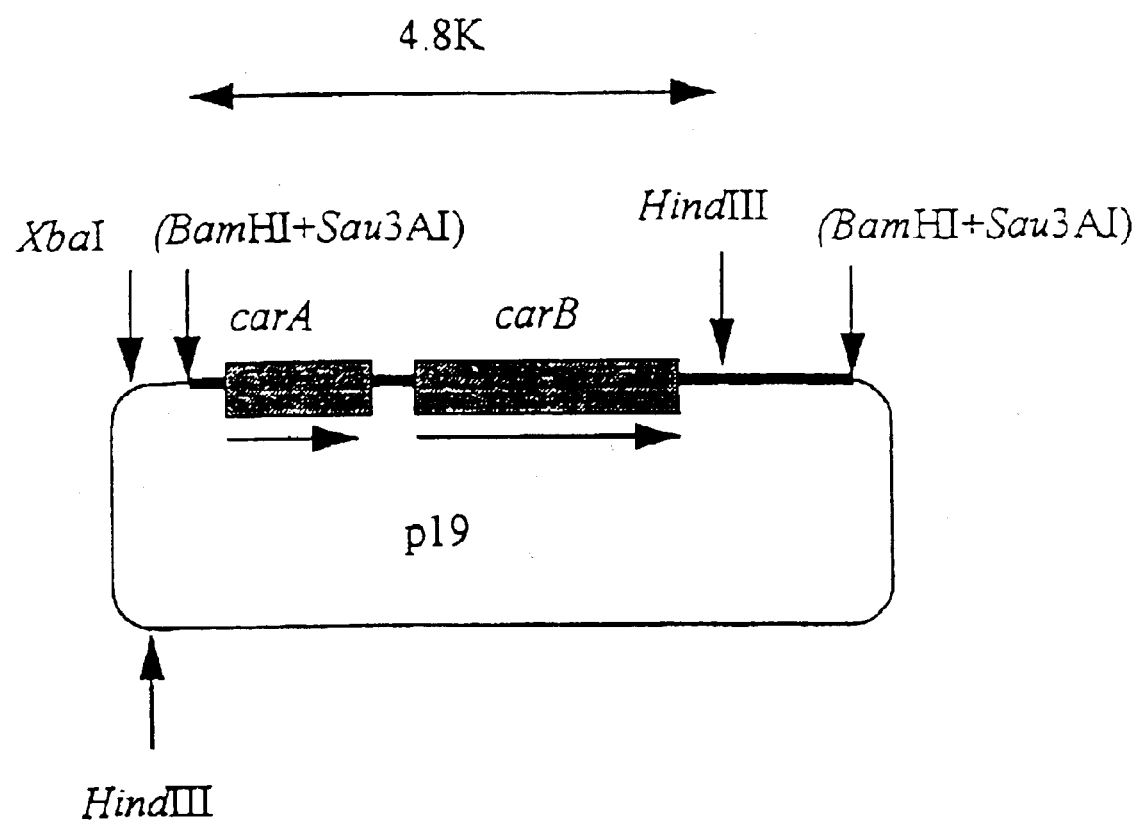
FIG. 1 shows the structure of plasmid p19 containing the carA gene and carB gene.

Hereafter, the present invention will be explained in detail.

<1> DNA of the Present Invention

The DNA of the present invention can be obtained from a chromosome DNA library of coryneform bacteria prepared with vectors such as plasmids by selection of the DNA using a microorganism which is deficient in carA or carB, for example, *Escherichia coli* RC50 (carA50, tsx⁻273, λ⁻, rpsL135 (str$^R$), malT1 (λR), xylA7, thi$^{31}$ 1; *Mol. Gen. Genet.*, 133, 299 (1974)), *Escherichia coli* JEF8 (thr⁻31, ΔcarB, relA⁻, metB1, *Mol. Gen. Genet.*, 133, 299 (1974)) and so forth. Because a microorganism which is deficient in carA or carB exhibits L-arginine and uracil auxotrophy, a DNA fragment can be obtained by transforming such a microorganism with a chromosome DNA library, selecting clones in which the auxotrophy is complemented, and recovering a recombinant vector from the selected transformants.

The coryneform bacteria used for preparing a chromosome DNA library are not particularly limited, and examples thereof include bacteria having been hitherto classified into the genus *Brevibacterium* but united into the genus *Corynebacterium* at present (Int. *J. Syst. Bacteriol.*, 41, 255 (1981)), and include bacteria belonging to the genus *Brevibacterium* closely relative to the genus *Corynebacterium*, more specifically, wild strains of *Brevibacterium lactofermentum* and so forth. Chromosome DNA of coryneform bacteria can be prepared by, for example, the method of Saito and Miura (*Biochem. Biophys. Acta.*, 72, 619, (1963)), the method of K. S. Kirby (*Biochem. J.*, 64, 405, (1956)) and so forth.

A chromosome DNA library can be obtained by partially digesting chromosome DNA with suitable restriction enzymes, ligating each of the obtained DNA fragments to a vector DNA autonomously replicable in *Escherichia coli* cells to prepare a recombinant DNA, and introducing the DNA into *Escherichia coli*. The vector is not particularly limited so long as it is a vector usually used for genetic cloning, and plasmid vectors such as pUC19, pUC18, pUC118, and pUC119, phage vectors such as λ phage DNA and so forth can be used. Further, a vector autonomously replicable in both of *Escherichia coli* cells and coryneform bacterium cells may also be used. Such a vector can be constructed by ligating a vector for *Escherichia coli* and pAM330, which is a cryptic plasmid of *Brevibacterium lactofermentum* (see Japanese Patent Laid-open No. 58-67699).

Specific examples of the vector autonomously replicable within both of *Escherichia coli* and coryneform bacterium cells include pSAC4 (see the examples mentioned below), pHK4 (see Japanese Patent Laid-open No. 5-7491) and so forth. *Escherichia coli* HB101 harboring pHK4 was designated as *Escherichia coli* AJ13136, and it was deposited at the National Institute of Bioscience and Human-Technology, Agency of Industrial Science and Technology, Ministry of International Trade and Industry (postal code 305-8566, 1-3 Higashi 1-chome, Tsukuba-shi, Ibaraki-ken, Japan) on Aug. 1, 1995, and received an accession number of FERM BP-5186.

The transformation of *Escherichia coli* cells can be performed by, for example, the method of D. A. Morrison (Methods in Enzymology, 68, 326, 1979), the method of treating recipient cells with calcium chloride so as to increase the permeability of DNA (Mandel, M. and Higa, A., *J. Mol. Biol.*, 53, 159 (1970)) and so forth. As for methods for preparation of chromosome DNA library, preparation of plasmid DNA, and digestion and ligation of DNA, as well as methods for PCR, preparation of oligonucleotides and hybridization mentioned hereinafter, conventional methods well known to those skilled in the art can be used. Such methods are described in Sambrook, J., Fritsch, E. F. and Maniatis, T., "Molecular Cloning, A Laboratory Manual, Second Edition", Cold Spring Harbor Laboratory Press, (1989) and so forth.

A nucleotide sequence of a DNA fragment containing carA and carB obtained as described above is represented as SEQ ID NO: 1 in Sequence Listing. This sequence contains two open reading frames (ORF, nucleotide numbers 283 to 1461and nucleotide numbers 1756 to 4809). The upstream ORF is carA, and the downstream ORF is carB. The amino acid sequences encoded by these ORFs are shown in SEQ ID NOS: 2 and 3, respectively. According to the present invention, a peptide encoded by carA is referred to as a small subunit, and a peptide encoded by carB is referred to as a large subunit. As for the coding region of carA, GTG of the nucleotide numbers 283 to 285 is indicated as the initiation codon in Sequence Listing. However, GTG of the nucleotide numbers 415 to 417 or ATG of the nucleotide numbers 430 to 432 may possibly be the initiation codon. In any case, an active small subunit can be obtained by using a longer open reading frame for the upstream region for the expression of carA. The amino acid corresponding to the GTG as the initiation codon is indicated as valine for each subunit, but it may be methionine, valine or formylmethionine.

The small subunit of the carbamoyl-phosphate synthetase of the present invention is, for example, a polypeptide having the amino acid sequence of the amino acid numbers 50 to 393 in SEQ ID NO: 2, polypeptide having the amino acid sequence of the amino acid numbers 45 to 393 in SEQ ID NO: 2, polypeptide having the amino acid sequence of the amino acid numbers 1 to 393 in SEQ ID NO: 2 or the like. The large subunit of the carbamoyl-phosphate synthetase of the present invention is, for example, a polypeptide having the amino acid sequence shown as SEQ ID NO: 3.

According to the present invention, the DNA coding for the small subunit may be one coding for an amino acid sequence which contains the amino acid sequence of the amino acid numbers 50 to 393 in SEQ ID NO: 2 including substitution, deletion, insertion, addition, or inversion of one or several amino acids, or one coding for a polypeptide which can constitute a protein having a carbamoyl-phosphate synthetase activity with the large subunit.

According to the present invention, the DNA coding for the large subunit may be one coding for an amino acid sequence which contains the amino acid sequence of SEQ ID NO: 3 including substitution, deletion, insertion, addition, or inversion of one or several amino acids, or one coding for a polypeptide which can constitute a protein having a carbamoyl-phosphate synthetase activity with the small subunit. Alternatively, it may be one coding for a protein which has the amino acid sequence of SEQ ID NO: 3 including substitution, deletion, insertion, addition, or inversion of one or several amino acids, and has a carbamoyl-phosphate synthetase activity.

Furthermore, a DNA that encodes carbamoyl-phosphate synthetase containing a mutation or mutations in the small subunit or the large subunit, or both of them also falls within the scope of the DNA of the present invention.

The term "several amino acids" preferably means 1 to 20 amino acids, more preferably 1 to 10 amino acids.

DNA, which encodes the substantially same peptide as the small subunit or the large subunit as described above, is obtained, for example, by modifying the nucleotide sequence of the DNA encoding the small subunit or the large subunit, for example, by means of the site-directed mutagenesis method so that one or more amino acid residues at a specified site of the gene involve substitution, deletion, insertion, addition, or inversion. DNA modified as described above may be obtained by the conventionally known mutation treatment. The mutation treatment includes a method for treating DNA coding for the small subunit or the large subunit in vitro, for example, with hydroxylamine, and a method for treating a microorganism, for example, a bacterium belonging to the genus *Escherichia* harboring DNA coding for the small subunit and the large subunit with ultraviolet irradiation or a mutating agent such as N-methyl-N'-nitro-N-nitrosoguanidine (NTG) and nitrous acid usually used for the mutation treatment.

The substitution, deletion, insertion, addition, or inversion of nucleotide as described above also includes mutation (mutant or variant) which naturally occurs, for example, the difference in strains, species or genera of the microorganism having the small subunit and/or the large subunit.

The DNA, which encodes substantially the same protein as carbamoyl-phosphate synthetase, is obtained by expressing DNA having mutation as described above in an appropriate cell, and investigating the carbamoyl-phosphate synthetase activity of an expressed product. The carbamoyl-phosphate synthetase activity can be measured by the known method (*Journal of Genral Microbiology*, 136, 1177–1183 (1990)). The DNA, which encodes substantially the same protein as carbamoyl-phosphate synthetase, is also obtained by isolating DNA which is hybridizable with DNA having, for example, a nucleotide sequence corresponding to nucleotide numbers of 283 to 1461 or 1756 to 4809 of the nucleotide sequence of SEQ ID NO: 2, under a stringent condition, and which encodes a protein having the carbamoyl-phosphate synthetase activity, from DNA coding for carbamoyl-phosphate synthetase having mutation or from a cell harboring it. The "stringent condition" referred to herein is a condition under which so-called specific hybrid is formed, and non-specific hybrid is not formed. It is difficult to clearly express this condition by using any numerical value. However, for example, the stringent condition includes a condition under which DNA's having high homology, for example, DNA's having homology of not less than 70%, preferably not less than 80%, more preferably not less than 90% are hybridized with each other, and DNA's having homology lower than the above are not hybridized with each other. Alternatively, the stringent condition is exemplified by a condition under which DNA's are hybridized with each other at a salt concentration corresponding to an ordinary condition of washing in Southern hybridization, i.e., 60° C., 1×SSC, 0.1% SDS, preferably 0.1×SSC, 0.1% SDS.

As a probe, a partial sequence of the nucleotide sequence of SEQ ID NO: 1 can also be used. Such a probe may be prepared by PCR using oligonucleotides produced based on the nucleotide sequence of SEQ ID NO: 1 as primers, and a DNA fragment containing the nucleotide sequence of SEQ ID NO: 1 as a template. When a DNA fragment in a length of about 300 bp is used as the probe, the conditions of washing for the hybridization consist of, for example, 50° C., 2×SSC, and 0.1% SDS.

Because the nucleotide sequence of the DNA of the present invention has been elucidated, the DNA of the present invention can be obtained by amplifying it from coryneform bacterial chromosome DNA through polymerase chain reaction (PCR: polymerase chain reaction; see White, T. J. et al., *Trends Genet.*, 5, 185 (1989)) utilizing oligonucleotides prepared based on that nucleotide sequence as primers, or by selecting it from a coryneform bacterial chromosome DNA library by hybridization utilizing an oligonucleotide prepared based on that nucleotide sequence as a probe. As nucleotide sequences of the primers used for PCR, a region upstream from the nucleotide number 283, preferably a region upstream from the nucleotide number 185 of SEQ ID NO: 1 can suitably be selected as the 5' primer, and a region downstream from the nucleotide number 4809 of SEQ ID NO: 1 can suitably be selected as the 3' primer.

Examples of the host for the expression of the DNA of the present invention include various bacteria such as *Escherichia coli* and coryneform bacteria including *Brevibacterium lactofermentum* and *Brevibacterium flavum*, eukaryotic cells such as those of *Saccharomyces cerevisiae* and so forth. In order to introduce the DNA of the present invention into these hosts, the host cells can be transformed with a recombinant vector obtained by inserting the DNA of the present invention into a vector selected according to the nature of the host in which the DNA is to be expressed. This procedure can be performed by a method well known to those skilled in the art. Specific examples of the method include the methods used for transformation of *Escherichia coli* mentioned above, the method in which competent cells are prepared from cells at the proliferating stage to introduce DNA, as reported for *Bacillus subtilis* (Duncan, C. H., Wilson, G. A. and Young, F. E., *Gene*, 1, 153 (1977)), the method in which DNA recipient cells are allowed to be in a state of protoplasts or spheroplasts capable of incorporating recombinant DNA with ease to introduce recombinant DNA into the DNA recipient cells, as known for *Bacillus subtilis*, actinomycetes, and yeasts (Chang, S. and Choen, S. N., *Molec. Gen. Genet.*, 168, 111 (1979); Bibb, M. J., Ward, J. M. and Hopwood, O. A., *Nature*, 274, 398 (1978); Hinnen, A., Hicks, J. B. and Fink, G. R., *Proc. Natl. Acad. Sci. USA*, 75, 1929 (1978)), the electric pulse method useful for cryneform bacteria (refer to Japanese Patent Publication Laid-Open No. 2-207791) and so forth.

The DNA to be introduced into the host such as those mentioned above may be DNA containing either carA or carB, or DNA containing both of them. Further, in order to attain efficient expression of these genes, a promoter functioning in the host cells such as lac, trp and $P_L$ may be ligated at a position upstream from carA or carB.

Carbamoyl-phosphate synthetase or its subunits can be produced by culturing a transformant such as those mentioned above under a condition that allows the expression of carA or carB. The DNA of the present invention can also be utilized for breeding of L-arginine-producing bacteria or nucleic acid-producing bacteria such as uracil-producing bacteria. That is, a transformant introduced with the DNA of the present invention, in particular, one introduced with either carA or carB or both of them, should have increased carbamoyl-phosphate synthetase activity compared with non-transformants. Consequently, its productivity for L-arginine or nucleic acid such as uracil is improved.

<2> Method for Producing L-Arginine According to the Present Invention

L-Arginine can efficiently be produced by culturing a microorganism that has enhanced intracellular carbamoyl-phosphate synthetase activity, and has L-arginine productivity in a medium to produce and accumulate L-arginine in the medium, and collecting the L-arginine from the medium.

Specific examples of the microorganism having L-arginine productivity include coryneform bacteria, bacteria belonging to the genera *Bacillus, Serratia* and *Escherichia*, yeast species belonging to the genus *Saccharomyces* or *Candida*. Of these, coryneform bacteria are preferred.

Exemplary specific species include *Bacillus subtilis* as a bacterium belonging to the genus *Bacillus, Serratia marcescens* as a bacterium belonging to the genus *Serratia, Escherichia coli* as a bacterium belonging to the genus *Escherichia, Saccharomyces cerevisiae* as a yeast species belonging to the genus *Saccharomyces, Candida tropicalis* as a yeast species belonging to the genus *Candida* and so forth.

Exemplary microorganisms having L-arginine productivity include *Bacillus subtilis* resistant to 5-azauracil, 6-azauracil, 2-thiouracil, 5-fluorouracil, 5-bromouracil, 5-azacytosine and so forth, *Bacillus subtilis* resistant to arginine hydroxamate and 2-thiouracil, *Bacillus subtilis* resistant to arginine hydroxamate and 6-azauracil (see Japanese Patent Laid-open No. 49-1268191),

*Bacillus subtilis* resistant to histidine analogues or tryptophan analogues (see Japanese Patent Laid-open No. 52-114092), a mutant of *Bacillus subtilis* exhibiting auxotrophy for at least one of methionine, histidine, threonine, proline, isoleucine, lysine, adenine, guanine and uracil (or uracil precursor) (see Japanese Patent Laid-open No. 52-99289),

*Bacillus subtilis* resistant to arginine hydroxamate (see Japanese Patent Publication No. 51-6754),

*Serratia marcescens* exhibiting succinic acid auxotrophy or resistance to nucleic acid base analogues (Japanese Patent Laid-open No. 58-9692),

*Serratia marcescens* deficient in ability to metabolize arginine and exhibiting resistance to arginine antagonists and canavanine and auxotorophy for lysine (see Japanese Patent Laid-open No. 52-8729),

*Escherichia coli* introduced with the argA gene (see Japanese Patent Laid-open No. 57-5693),

*Saccharomyces cerevisiae* resistant to arginine, arginine hydroxamate, homoarginine, D-arginine and canavanine, or resistant to arginine hydroxamate and 6-azauracil (see Japanese Patent Laid-open No. 53-143288),

*Candida tropicalis* resistant to canavanine (see Japanese Patent Laid-open No. 53-3586) and so forth.

Coryneform bacteria include those bacteria having been hitherto classified into the genus *Brevibacterium* but united into the genus *Corynebacterium* at present (*Int. J. Syst. Bacteriol.*, 41, 255 (1981)), and include bacteria belonging to the genus *Brevibacterium* closely relative to the genus *Corynebacterium*. Examples of such coryneform bacteria are listed below.

*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium* (*Corynebacterium glutamicum*)

*Corynebacterium melassecola*
*Corynebacterium thermoaminogenes*
*Corynebacterium herculis*
*Brevibacterium divaricatum*
(*Corynebacterium glutamicum*)
*Brevibacterium flavum* (*Corynebacterium glutamicum*)
*Brevibacterium immariophilum*
*Brevibacterium lactofermentum*
(*Corynebacterium glutamicum*)
*Brevibacterium roseum*
*Brevibacterium saccharolyticum*
*Brevibacterium thiogenitalis*
*Brevibacterium album*
*Brevibacterium cerinum*
*Microbacterium ammoniaphilum*

The coryneform bacteria that have the L-arginine productivity are not particularly limited so long as they have the L-arginine productivity. They include, for example, wild-type strains of coryneform bacteria; coryneform bacteria resistant to certain agents including sulfa drugs, 2-thiazolealanine, α-amino-β-hydroxyvaleric acid and the like; coryneform bacteria exhibiting L-histidine, L-proline, L-threonine, L-isoleucine, L-methionine, or L-tryptophan auxotrophy in addition to the resistance to 2-thiazolealanine (Japanese Patent Laid-open No. 54-44096); coryneform bacteria resistant to ketomalonic acid, fluoromalonic acid, or monofluoroacetic acid (Japanese Patent Laid-open No. 57-18989); coryneform bacteria resistant to argininol (Japanese Patent Laid-open No. 62-24075); coryneform bacteria resistant to X-guanidine (X represents a derivative of fatty acid or aliphatic chain, Japanese Patent Laid-open No. 2-186995) and so forth.

Specifically, the following bacterial strains can be exemplified.

*Brevibacterium flavum* AJ11169 (FERM BP-6892)
*Brevibacterium lactofermentum* AJ12092 (FERM BP-6906)
*Brevibacterium flavum* AJ11336 (FERM BP-6893)
*Brevibacterium flavum* AJ11345 (FERM BP-6893)
*Brevibacterium lactofermentum* AJ12430 (FERM BP-2228)

The AJ11169 strain and the AJ12092 strain are the 2-thiazolealanine resistant strains mentioned in Japanese Patent Laid-open No. 54-44096, the AJ11336 strain is the strain having argininol resistance and sulfadiazine resistance mentioned in Japanese Patent Publication No. 62-24075, the AJ11345 strain is the strain having argininol resistance, 2-thiazolealanine resistance, sulfaguanidine resistance, and exhibiting histidine auxotrophy mentioned in Japanese Patent Publication No. 62-24075, and the AJ12430 strain is the strain having octylguanidine resistance and 2-thiazolealanine resistance mentioned in Japanese Patent Laid-open No. 2-186995.

The intracellular carbamoyl-phosphate synthetase activity of such microorganisms having the L-arginine productivity as mentioned above can be enhanced by, for example, increasing copy number of a gene coding for the carbamoyl-phosphate synthetase in the cells of the aforementioned microorganisms. The enhancement of the carbamoyl-phosphate synthetase activity can also be achieved by, in addition to the aforementioned gene amplification, modifying an expression regulation sequence for the DNA coding for carbamoyl-phosphate synthetase so that expression of the DNA gene coding for carbamoyl-phosphate synthetase should be enhanced. Specifically, an expression regulation sequence such as a promoter for a gene coding for carbamoyl-phosphate synthetase on the chromosomal DNA or a plasmid can be replaced with a stronger one (see Japanese Patent Laid-open No. 1-215280). Strong promoters, which function in cells of coryneform bacteria, include lac promoter, tac promoter, trp promoter, of *Escherichia coli* (Y. Morinaga, M. Tsuchiya, K. Miwa and K. Sano, J. Biotech., 5, 305–312 (1987)) and the like. In addition, trp promoter of *Corynebacterium* bacteria is also a preferable promoter (Japanese Patent Laid-open No. 62-195294). By the replacement with these promoters the carbamoyl-phosphate synthetase activity is enhanced. The modification of expression regulation sequence may be combined with the increasing of the copy number of DNA coding for carbamoyl-phosphate synthetase. Further, the intracellular carbamoyl-phosphate synthetase activity can be enhanced by introducing one or more mutations into the enzyme protein of carbamoyl-phosphate synthetase so that the specific activity of the enzyme should be increased.

Examples of the DNA coding for carbamoyl-phosphate synthetase include the aforementioned carA and carB genes of *Brevibacterium lactofermentum* and one containing both of them.

Examples of the vector for introducing DNA coding for carbamoyl-phosphate synthetase into a microorganism include vectors autonomously replicable in cells of the microorganism. Specifically, the aforementioned vectors autonomously replicable in *Escherichia coli* cells, and the vectors autonomously replicable in both of *Escherichia coli* cells and coryneform bacterium cells.

The medium used for culturing a microorganism having enhanced intracellular carbamoyl-phosphate synthetase activity and L-arginine productivity obtained as described above may be a well-known medium conventionally used for the production of amino acids by fermentation. That is, it is a usual medium that contains a carbon source, nitrogen source, inorganic ions, and other organic components as required.

As the carbon source, it is possible to use sugars such as glucose, sucrose, lactose, galactose, fructose and starch hydrolysates; alcohols such as glycerol and sorbitol; or organic acids such as fumaric acid, citric acid and succinic acid and so forth.

As the nitrogen source, it is possible to use inorganic ammonium salts such as ammonium sulfate, ammonium chloride and ammonium phosphate, organic nitrogen such as soybean hydrolysates, ammonia gas, aqueous ammonia and so forth.

The medium preferably contains a suitable amount of required substance such as vitamin $B_1$ and L-homoserine, yeast extract and so forth as trace amount organic nutrients. Other than those substances, a small amount of potassium phosphate, magnesium sulfate, iron ions, manganese ions and so forth may be added to the medium.

The cultivation is preferably performed under an aerobic condition for 1–7 days. Cultivation temperature is preferably 24–37° C., and pH of the medium during the cultivation is preferably 5–9. Inorganic or organic acidic or alkaline substances, ammonia gas and so forth may be used for adjusting pH. L-Arginine can usually be recovered from the fermentation medium by a combination of known techniques such as ion exchange resin method.

BEST MODE FOR CARRYING OUT THE INVENTION

Hereafter, the present invention will be explained more specifically with reference to the following examples.

EXAMPLE 1

Cloning of carA and carB of *Brevibacterium lactofermentum*

<1> Preparation of Chromosome DNA of *Brevibacterium lactofermentum* ATCC13869

*Brevibacterium lactofermentum* ATCC13869 was inoculated to 100 ml of T-Y culture medium (1% of Bacto-Trypton (Difco), 0.5% of Bacto-Yeast Extract (Difco), 0.5% of NaCl (pH 7.2)), and cultured at a temperature of 31.5° C. for 8 hours to obtain a culture. The culture was centrifuged at 3,000 r.p.m. for 15 minutes to obtain 0.5 g of wet bacterial cells, and chromosome DNA was obtained from the bacterial cells according to the method of Saito and Miura (*Biochem. Biophys. Acta.*, 72, 619 (1963)). Then, 60 μg of the chromosome DNA and 3 units of restriction enzyme Sau3AI were each mixed in 10 mM Tris-HCl buffer (containing 50 mM NaCl, 10 mM $MgSO_4$ and 1 mM dithiothreitol (pH 7.4)), and allowed to react at a temperature of 37° C. for 30 minutes. The reaction mixture was subjected to phenol extraction and ethanol precipitation in a conventional manner to obtain 50 μg of chromosome DNA fragments of *Brevibacterium lactofermentum* ATCC13869 digested with Sau3AI.

<2> Preparation of Gene Library of *Brevibacterium lactofermentum* ATCC13869 Using Plasmid Vector DNA As a plasmid vector DNA autonomously replicable in both of *Escherichia coli* cells and coryneform bacterium cells, pSAC4 was used. pSAC4 was prepared as follows. In order to make a vector pHSG399 for *Escherichia coli* (Takara Shuzo) autonomously replicable in coryneform bacterium cells, a replication origin of the previously obtained plasmid pHM1519 autonomously replicable in coryneform bacterium cells (Miwa, K. et al., *Agric. Biol. Chem.*, 48 (1984) 2901–2903) was introduced into the vector (Japanese Patent Laid-open No. 5-7491). Specifically, pHM1519 was digested with restriction enzymes BamHI and KpnI to obtain a gene fragment containing the replication origin, and the obtained fragment was blunt-ended by using Blunting Lit produced by Takara Shuzo, and inserted into the SalI site of pHSG399 using a SalI linker (produced by Takara Shuzo) to obtain pSAC4.

In 50 mM Tris-HCl buffer (containing 100 mM NaCl and 10 mM magnesium sulfate (pH 7.4)), 20 μg of pSAC4 and 200 units of a restriction enzyme BamHI were mixed, and allowed to react at a temperature of 37° C. for 2 hours to obtain a digestion solution. This solution was subjected to phenol extraction and ethanol precipitation in a conventional manner. Then, in order to inhibit re-ligation of the DNA fragments derived from the plasmid vector, the DNA fragments were dephosphorylated with bacterial alkaline phosphatase according to the method described in Molecular Cloning, 2nd Edition (J. Sambrook, E. F. Fritsch and T. Maniatis, Cold Spring Harbor Laboratory Press, p1.56 (1989)), and subjected to phenol extraction and ethanol precipitation in a conventional manner.

To 66 mM Tris-HCl buffer (pH 7.5) containing 66 mM magnesium chloride, 10 mM dithiothreitol and 10 mM ATP, 1 μg of the pSAC4 digested with BamHI, 1 μg of the chromosome DNA fragments of *Brevibacterium lactofermentum* ATCC13869 digested with Sau3AI obtained in Example 1, and 2 units of T4 DNA ligase (produced by Takara Shuzo) were added, and allowed to react at a temperature of 16° C. for 16 hours to ligate the DNA. Then, *Escherichia coli* DH5 was transformed with this DNA mixture in a conventional manner, and plated on an L agar medium containing 170 μg/ml of chloramphenicol to obtain about 20,000 colonies, which were used as a gene library.

<3> Transformation of carB-Deficient Strain of *Escherichia coli* (JEF8)

The carB-deficient strain of *Escherichia coli*, JEF8 (thr$^{31}$31, ΔcarB, relA$^{31}$, metB1; *Mol. Gen. Genet.*, 133, 299 (1974)) was transformed with a recombinant DNA mixture of the aforementioned gene library in a conventional manner. Transformants of about 15000 strains were obtained as Cm resistant strains. These transformants were replicated on a minimum medium (5 g/L of glucose, 12.8 g/L of $Na_2HPO_4$, 3 g/L of $KH_2PO_4$, 0.5 g/L of NaCl, 1 g/L of $NH_4Cl$, 40 μg/ml of L-threonine, 40 μg/ml of L-methionine) not containing arginine and uracil, and the minimum medium not containing L-arginine, but containing only 50 μg/ml of uracil, and screened for a strain in which arginine auxotrophy and uracil auxotrophy were restored, or a strain in which arginine auxotrophy was restored. Strains in which arginine auxotrophy was restored recovered both of arginine auxotrophy and uracil auxotrophy. A plasmid harbored in one of such strains was designated as p19, and the strain harboring it was designated as JEF8/p19. The structure of p19 is shown in FIG. 1.

The *Escherichia coli* JEF8/p19 was designated as *Escherichia coli* AJ13574, and it was deposited at the National Institute of Bioscience and Human-Technology, Agency of Industrial Science and Technology, Ministry of International Trade and Industry (postal code 305-8566, 1-3 Higashi 1-chome, Tsukuba-shi, Ibaraki-ken, Japan) on Jan. 28, 1999, and received an accession number of FERM P-17180, and transferred from the original deposit to international deposit based on Budapest Treaty on Jan. 6, 20000, and has been deposited as deposition number of FERM BP-6989.

<4> Acquisition of Plasmid Complementing Arginine and Uracil Auxotrophy

A plasmid was prepared from JEF8/p19 in a conventional manner, and used for re-transformation of the JEF8 strain. The obtained transformants could grow in the minimum culture medium not containing L-arginine and uracil, and its auxotrophy for both of L-arginine and uracil was restored. Therefore, it was found that that the plasmid contained a gene complementing the auxotrophy for both of L-arginine and uracil caused by deletion of carB in the *Escherichia coli* strain.

Further, this plasmid was introduced into the carA mutant of *Escherichia coli*, RC50 (carA50, tsx$^-$273, λ$^-$, rpsL135 (str$^R$) malT1 (λR), xylA7, thi$^-$1; *Mol. Gen. Genet.*, 133, 299 (1974)). Since the strain introduced with the plasmid was able to grow in the minimum culture medium not containing arginine and uracil, the plasmid was also found to have a gene complementing the auxotrophy for both of L-arginine and uracil caused by carA mutation of the *Escherichia coli* strain.

<5> Nucleotide Sequence Analysis of p19

Among the DNA sequence of p19, the nucleotide sequence of about 4.8 kb from the HindIII side of the multi-cloning site of the vector to the HindIII site contained in the insertion DNA fragment was determined. The nucleotide sequencing was performed by using Rohdamin Terminator Cycle Sequencing Kit (produced by ABI) according to the method of Sanger. The obtained nucleotide sequence is shown as SEQ ID NO: 1 in Sequence Listing. From analysis of a consensus sequence which located in the upstream region of this gene, it was estimated that two open reading frames (open reading frame from 283rd G to 1461st A and open reading frame from 1756th G to 4809th T) were contained in this sequence. The nucleotides of the 162nd (TGCATA) to 194th (TATAAT), the 185th (TGCATA) to 213rd (TAAACT), the 203rd (TTGAAT) 230th (TATCAA), or the 224th (TTATCA) to 251st (TAAAAA) can be estimated to be a promoter region for regulating the transcription.

The amino acid sequences encoded by these open reading frames are represented with the nucleotide sequences. The amino acid sequences were also shown in SEQ ID NOS: 2 and 3. A protein database (GenBank CDS) was searched for sequences exhibiting homology with these amino acid sequences. As a result, it was found that the 5' open reading frame showed high homology (about 40%) with carA gene products of *Escherichia coli, Bacillus subtilis* and so forth, and the 3' open reading frame showed high homology with known carB gene products of *Escherichia coli, Bacillus stearothermophilus* and so forth (about 40 to 50%). Therefore, it was suggested that these open reading frames coded for carA and carB, respectively.

<6>Introduction of carA and carB into Wild-Type Strain of Coryneform Bacteria p19 was introduced into the *Brevibacterium flavum* wild strain 2247 (AJ14067) by the electric pulse method (Japanese Patent Laid-open No. 2-207791). The transformants were selected as chloramphenicol resistant strains on a CM2G plate medium (containing 10 g of polypeptone, 10 g of yeast extract, 5 g of glucose, 5 g of NaCl, 15 g of agar in 1 L of pure water, pH 7.2) containing 5 µg/ml of chloramphenicol to obtain 2247/p19.

EXAMPLE 2

Production of L-Arginine by Coryneform Bacteria Introduced with carA and carB

<1> Preparation of Shuttle Vector

First, a plasmid vector autonomously replicable in both of *Escherichia coli* cells and coryneform bacterium cells was newly produced as a plasmid used for introducing the carA and carB genes into coryneform bacteria.

A vector containing a drug resistance gene of *Streptococcus faecalis* was constructed first. The kanamycin resistant gene of *Streptococcus faecalis* was amplified by PCR from a known plasmid containing that gene. The nucleotide sequence of the kanamycin resistant gene of *Streptococcus faecalis* has already been clarified (Trieu-Cuot, P. and Courvalin, P., Gene, 23(3), 331–341 (1983)). The primers shown as SEQ ID NOS: 4 and 5 were synthesized based on that sequence, and PCR was performed by using pDG783 (Anne-Marie Guerout-Fleury et al., Gene, 167, 335–337 (1995)) as a template to amplify a DNA fragment containing the kanamycin resistant gene and its promoter.

The obtained DNA fragment was purified by SUPREC02 produced by the Takara Shuzo, then fully digested with restriction enzymes HindIII and HincII, and blunt-ended. The blunt-ending was attained by using Blunting Kit produced by Takara Shuzo. This DNA fragment was mixed with and ligated to a DNA fragment, which had been obtained by performing PCR using the primers shown as SEQ ID NOS: 6 and 7 and pHSG399 (see S. Takeshita et al., Gene, 61, 63–74 (1987)) as a template, purifying and blunt-ending the resulted amplification product. The ligation reaction was performed by DNA Ligation Kit ver. 2 produced by Takara Shuzo. Competent cells of *Escherichia coli* JM109 (produced by Takara Shuzo) were transformed with the ligated DNA, plated on L madium (10 g/L of Bacto-trypton, 5 g/L of Bacto-yeast extract, 5 g/L of NaCl, 15 g/L of agar, pH 7.2) containing 10 µg/ml of IPTG (isopropyl-β-D-thiogalactopyranoside), 40 µg/ml of X-Gal (5-bromo-4-chloro-3-indolyl-β-D-galactoside) and 25 µg/ml of kanamycin, and cultured overnight. The emerged blue colonies were picked up, and separated into single colonies to obtain transformant strains.

Figure 2:
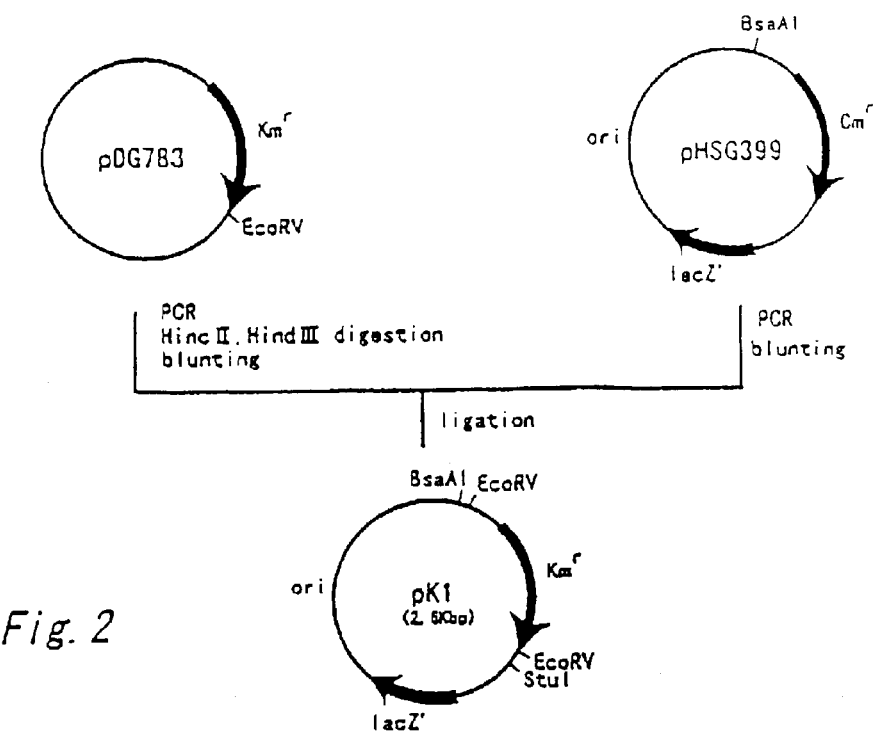
FIG. 2 shows a construction process of plasmid pK1.

Plasmids were prepared from the transformant strains by the alkali method (Text for bioengineering Experiments, Edited by Society for Bioscience and Bioengineering, Japan, p. 105, Baifukan, 1992), and restriction maps were prepared. One having a restriction map equivalent to that of FIG. 2 was designated as pK1. This plasmid is stably retained in *Escherichia coli*, and imparts kanamycin resistance to a host. Moreover, since it contains the lacZ' gene, it is suitably used as a cloning vector.

Figure 3:
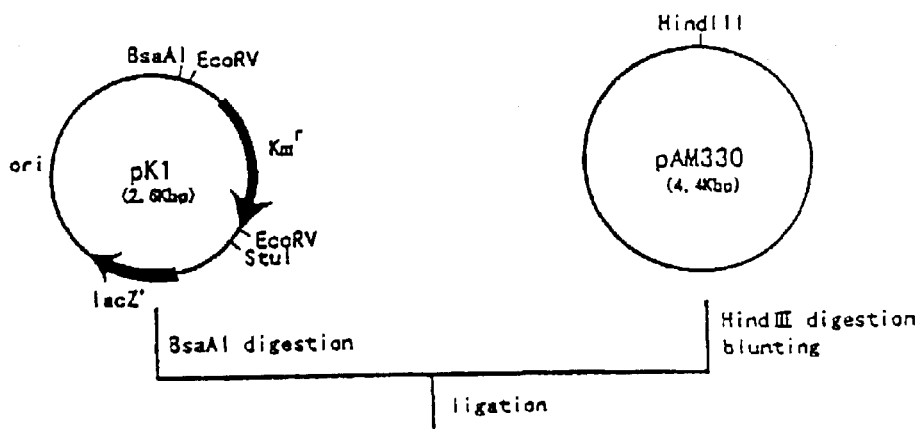
FIG. 3 shows a construction process of plasmid pSFK6.
Figure 3:
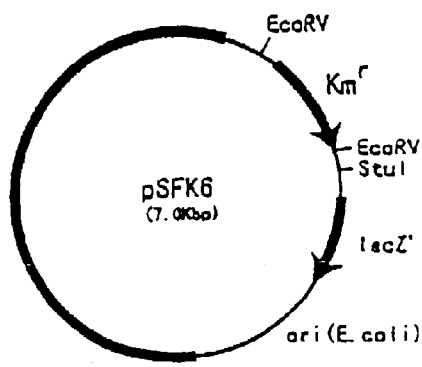

The plasmid pAM330 extracted from *Brevibacterium lactofermentum* ATCC13869 (see Japanese Patent Laid-open No. 58-67699) was fully digested with a restriction enzyme HindIII, and blunt-ended. This fragment was ligated to a fragment obtained by fully digesting the aforementioned pK1 with a restriction enzyme BsaAI. *Brevibacterium lactofermentum* ATCC13869 was transformed with the ligated DNA. The transformation was performed by the electric pulse method (see Japanese Patent Laid-open No. 2-207791). Transformants were selected on a M-CM2B plate (10 g/L of polypeptone, 10 g/L of yeast extract, 5 g/L of NaCl, 10 µg/L of biotin, 15 g/L of agar, pH 7.2) containing 25 µg/ml of kanamycin. After cultivation for 2 days, colonies were picked up, and separated into single colonies to obtain the transformants. Plasmid DNA was prepared from the transformants, and restriction maps were prepared. One having the same restriction map as that of FIG. 3 was designated as pSFK6. This plasmid can autonomously replicate in both of *Escherichia coli* and coryneform bacteria, and imparts kanamycin resistance to a host.

<2> Introduction of carA and carB Genes into Coryneform Bacteria and Production of L-Arginine The aforementioned pSFK6 was digested with SmaI and HindIII. The product was ligated to carA and carB gene fragments, which had been obtained by digesting the plasmid p19 prepared from JEF8/p19F in a conventional manner with a restriction enzyme XbaI, blunt-ending the product by using Blunting Kit produced by Takara Shuzo, and further digesting the product with a restriction enzyme HindIII, to obtain a plasmid pcarAB, which contained the carA and carB genes and could autonomously replicate in coryneform bacteria.

pcarAB was introduced into *Brevibacterium flavum* AJ11345 and AJ11336 by the electric pulse method (Japanese Patent Laid-open No. 2-207791). Transformants were selected on a M-CM2B plate (10 g/L of polypeptone, 10 g/L of yeast extract, 5 g/L of glucose, 5 g/L of NaCl, 15 g/L of agar, pH 7.2) containing 25 µg/ml of kanamycin as kanamycin resistant strains. As control, transformants were obtained by similarly introducing pSFK6 into AJ11345 and AJ11336.

Each of the aforementioned transformants was plated on an agar medium containing 0.5 g/dl of glucose, 1 g/dl of polypeptone, 1 g of yeast extract, 0.5 g/dl of NaCl and 5 µg/l of chloramphenicol, and cultured at 31.5° C. for 20 hours. One inoculating loop of the obtained cells were inoculated to a medium containing 4 g/dl of glucose, 6.5 g/dL of ammonium sulfate, 0.1 g/dl of $KH_2PO_4$, 0.04 g/dl of $MgSO_4$, 0.001 g/dl of $FeSO_4$, 0.01 g/dl of $MnSO_4$, 5 µg/dl of $VB_1$, 5 µg/dl of biotin, 45 mg/dl of soybean hydrolysates (as an amount of N), and cultured in a flask at 31.5° C. for 50 hours with shaking. The amounts of L-arginine produced by each strain were shown in Table 1.

The strains introduced with the carA and carB gene showed improved L-arginine productivity compared with the strains introduced only with the vector.

TABLE 1

| Strain/plasmid | L-arginine (g/dl) |
| --- | --- |
| AJ11345/pSFK6 | 1.33 |
| AJ11345/pcarAB | 1.39 |
| AJ11336/pSFK6 | 0.71 |
| AJ11336/pcarAB | 0.79 |

What is claimed is:

1. An isolated protein which comprises a polypeptide:
   (a) a polypeptide which has an amino acid sequence comprising at least the amino acid numbers 50 to 393 in SEQ ID NO: 2;
   (b) a polypeptide which is encoded by a polynucleotide sequence which hybridizes under stringent conditions to nucleotides 283–1461 of SEQ ID NO: 1 wherein said stringent conditions comprise washing at 60° C. in 1×SSC and 0.1% SDS, and wherein said polypeptide constitutes a protein having a carbamoyl-phosphate synthetase activity with a large subunit of carbamoyl-phosphate synthetase comprising the amino acid sequence of SEQ ID NO: 3;
   (c) a polypeptide which comprises the amino acid sequence of SEQ ID NO: 3; and
   (d) a polypeptide which is encoded by a polynucleotide sequence which hybridizes under stringent conditions to nucleotides 1470–4808 of SEQ ID NO: 1 wherein said stringent conditions comprise washing at 60° C. in 1×SSC and 0.1% SDS, and wherein said polypeptide constitutes a protein having a carbamoyl-phosphate synthetase activity with a small subunit of carbamoyl-phosphate synthetase having an amino acid sequence comprising at least the amino acid residues 50 to 393 of in SEQ ID NO: 2.

2. The isolated protein according to claim 1, wherein said polypeptide is the polypeptide defined in (a).

3. The isolated protein according to claim 1, wherein said polypeptide is the polypeptide defined in (b).

4. The isolated protein according to claim 3, wherein the polypeptide has the amino acid sequence encoded by the second open reading frame of *Brevibacterium lactofermentum* DNA contained in the plasmid p19 in *Escherichia coli* AJ13574 (FERM BP-6989).

5. The isolated protein according to claim 1, wherein said polypeptide is the polypeptide defined in (c).

6. The isolated protein according to claim 1, wherein said polypeptide is the polypeptide defined in (d).

* * * * *